US00RE49091E

(19) United States
(12) Reissued Patent
Fourt et al.

(10) Patent Number: US RE49,091 E
(45) Date of Reissued Patent: Jun. 7, 2022

(54) AUTOMATIC INJECTION DEVICE AND A BUTTON THEREOF

(71) Applicant: Eli Lilly and Company, Indianapolis, IN (US)

(72) Inventors: Jesse Arnold Fourt, Menlo Park, CA (US); Thomas Dieter Christian Overthun, San Francisco, CA (US); Judy Guo, San Francisco, CA (US); Thomas Gaëtan Thibault Brisebras, San Francisco, CA (US)

(73) Assignee: Eli Lilly and Company, Indianapolis, IN (US)

(21) Appl. No.: 29/672,419

(22) Filed: Dec. 5, 2018

Related U.S. Patent Documents

Reissue of:
(64) Patent No.: Des. 773,650
Issued: Dec. 6, 2016
Appl. No.: 29/530,811
Filed: Jun. 19, 2015

(51) LOC (13) Cl. ..... 24-02
(52) U.S. Cl.
USPC ..... D24/113
(58) Field of Classification Search
USPC ..... D24/112, 113, 114, 108, 127, 130, 133
(Continued)

(56) References Cited

U.S. PATENT DOCUMENTS

D192,757 S * 5/1962 Foss et al. ..... D9/452
D201,320 S * 6/1965 Hirohama ..... D9/453
(Continued)

FOREIGN PATENT DOCUMENTS

WO 2007002052 1/2007
WO 2007047200 4/2007
(Continued)

OTHER PUBLICATIONS

Ypsomed-YpsoMate® Brochure.
(Continued)

*Primary Examiner* — Philip S Hyder
(74) *Attorney, Agent, or Firm* — M. Daniel Spillman

(57) CLAIM

The ornamental design for an automatic injection device *and a button thereof*, as shown and described.

DESCRIPTION

*This is a reissue of U.S. Design Pat. No. D. 773,650, which issued on Dec. 6, 2016, from U.S. Design patent application Ser. No. 29/530,811, filed Jun. 19, 2015. The entire contents of U.S. application Ser. No. 29/530,811. and U.S. Pat No. D. 773,650 are incorporated herein by reference.*

*Notice: More than one reissue application has been filed for the reissue of U.S. Pat. No. D. 773,650. The reissue applications are U.S. application Ser. No. 29/674,238, U.S. application Ser. No. 29/674,241, U.S. application Ser. No. 29/674,243, U.S. application Ser. No. 29/674,244, and parent reissue U.S. application Ser. No. 29/672,419 (the present application), all of which are reissues of U.S. Pat. No. D. 773,650.*

FIG. 1 is a top perspective view of an automatic injection device showing our new design;
FIG. 2 is a bottom perspective view thereof[:]*;*
FIG. 3 is a front view thereof;
FIG. 4 is a rear view thereof;
FIG. 5 is side view thereof;
FIG. 6 is an opposite side view thereof;
FIG. 7 is a top view thereof; [and.]
FIG. 8 is a bottom view thereof[.]*;*
*FIG. 9 is a top perspective view of second embodiment of a button for an automatic injection device showing our new design;*
*FIG. 10 is a bottom perspective view thereof;*
*FIG. 11 is a front view thereof;*
*FIG. 12 is a rear view thereof;*
*FIG. 13 is side view thereof;*
*FIG. 14 is an opposite side view thereof;*
(Continued)

*(Amended)* *(New)*

*FIG. 15 is a top view thereof;*
*FIG. 16 is a bottom view thereof; and,*
*FIG. 17 is an enlarged, top perspective view, as shown in FIG. 9.*

The small ovals in the central height region of FIGS. 1-6 show projecting texturing that form part of the claimed design. The broken lines showing internal portions and a bottom portion of the automatic injection device form no part of the claimed design.

1 Claim, 11 Drawing Sheets

Figure 2:
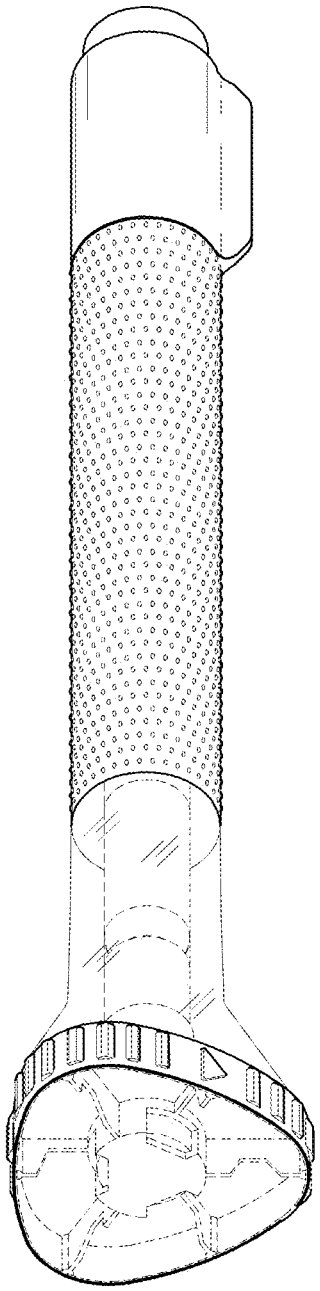
Figure 3:
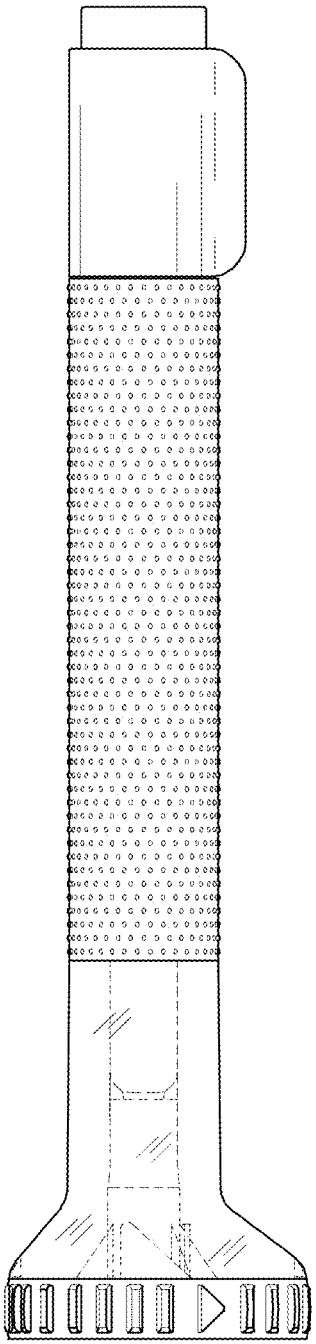
Figure 4:
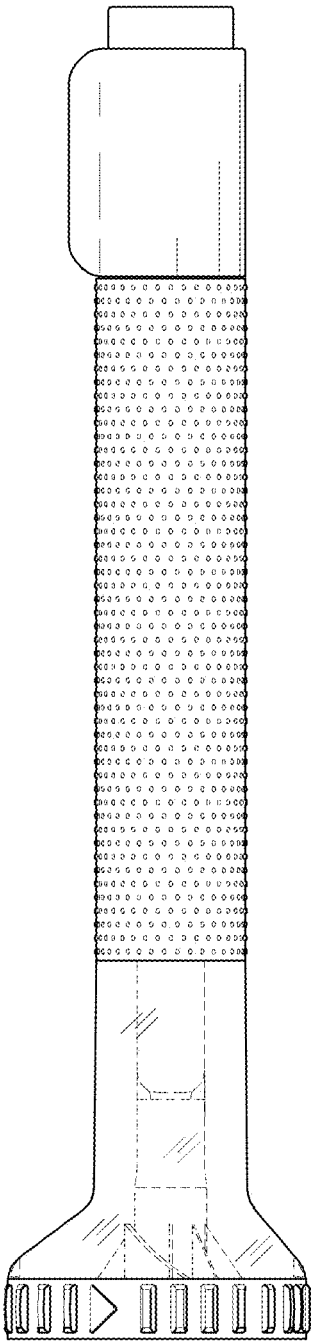
Figure 5:
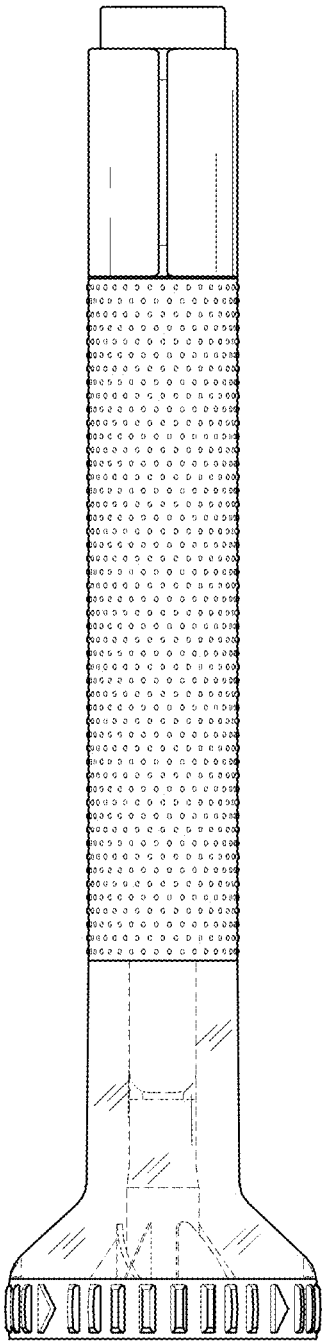
Figure 6:
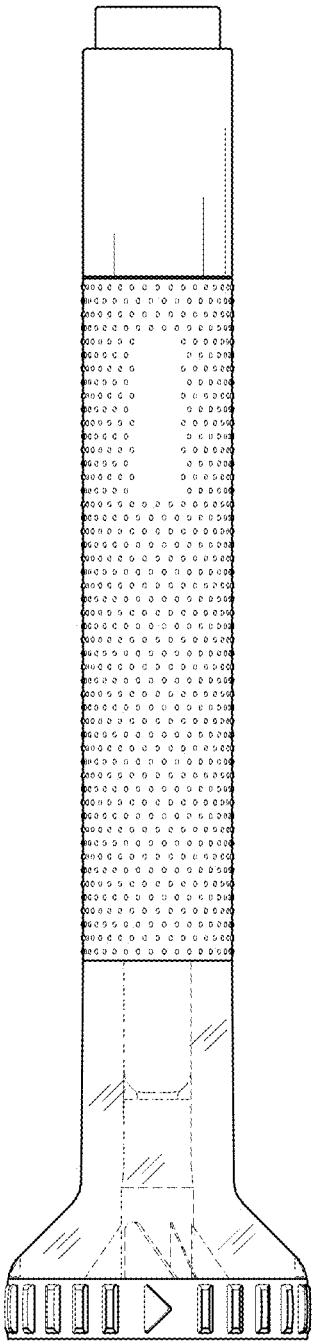
Figure 8:
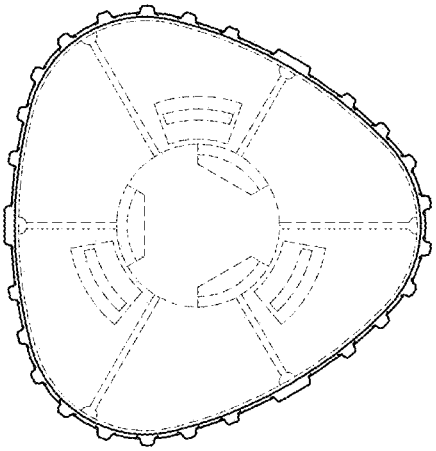

Matter enclosed in heavy brackets [ ] appears in the original patent but forms no part of this reissue; matter printed in italics indicates the additions made by reissue.

(58) Field of Classification Search
CPC ..... A61M 5/178; A61M 3/00; A61M 5/20; A61M 5/31; A61M 5/3146; A61M 5/3129; A61M 5/3148; A61M 5/315
See application file for complete search history.

(56) References Cited

U.S. PATENT DOCUMENTS 3,251,372 A * 5/1966 Smith ..... A45B 9/04 135/86
4,630,626 A * 12/1986 Urban ..... A45B 9/04 135/84
D291,371 S * 8/1987 Stutzer ..... D27/141
D310,324 S * 9/1990 Bernacchi ..... D8/352
D316,899 S 5/1991 Andersson et al.
D330,079 S 10/1992 Dalling et al.
D362,841 S * 10/1995 Roza ..... D13/171
D379,922 S * 6/1997 Adams ..... D8/402
5,711,335 A * 1/1998 Carpinella ..... A45B 9/04 135/77
5,743,506 A * 4/1998 Adams ..... A47B 91/00 248/346.11
D409,878 S * 5/1999 Burton ..... D7/410
D420,739 S 2/2000 Moreau-Defarges
6,055,998 A * 5/2000 Bader ..... A61H 3/0277 135/68
D437,835 S * 2/2001 Decosse ..... D13/174
D461,555 S * 8/2002 Binet ..... D24/114
D469,411 S * 1/2003 Decosse ..... D13/171
D471,976 S 3/2003 Pavlu et al.
D476,078 S 6/2003 Pavlu et al.
D476,734 S 7/2003 Pavlu et al.
D483,116 S 12/2003 Castellano
7,159,830 B2 * 1/2007 Frank ..... A45B 9/02 135/70
D572,586 S * 7/2008 Medema ..... D9/445
D594,270 S * 6/2009 Rae ..... D7/354
7,748,396 B2 * 7/2010 Lasota ..... A61H 3/0288 135/77
D628,690 S 12/2010 Galbraith
7,918,824 B2 4/2011 Bishop et al.
D642,057 S * 7/2011 Reed ..... D9/453
D670,375 S 11/2012 Corbin
D670,376 S 11/2012 Corbin
D677,380 S 3/2013 Julian et al.
8,409,138 B2 4/2013 James et al.
D690,416 S * 9/2013 Cappello ..... D24/112
D695,892 S * 12/2013 Cappello ..... D24/113
D696,397 S 12/2013 Guarraia et al.
D708,317 S 7/2014 Schneider et al.
D714,932 S * 10/2014 Hall ..... D24/112
D721,802 S * 1/2015 Ohashi ..... D24/113
D724,721 S 3/2015 Geert-Jensen et al.
D728,782 S 5/2015 Dubuc et al.
D729,930 S 5/2015 Geert-Jensen et al.
D732,161 S * 6/2015 Ohashi ..... D24/113
D739,011 S * 9/2015 Morrison, Jr. ..... D24/114
D740,221 S * 10/2015 Popper ..... D13/103
D741,472 S * 10/2015 Yotani ..... D24/108
D743,560 S * 11/2015 Pietrantonio ..... D24/186
D747,476 S * 1/2016 Kawamura ..... D24/130
D747,797 S * 1/2016 Fourt ..... D24/114
D748,270 S * 1/2016 Pietrantonio ..... D24/186
D752,210 S * 3/2016 Amend Kwasnik ..... D24/113
D753,950 S * 4/2016 Feeley ..... D7/392.1
D758,570 S * 6/2016 Wohlfahrt ..... D24/113
D773,646 S * 12/2016 Amend Kwasnik ..... D24/113
D804,230 S * 12/2017 Allan ..... D6/716
D824,763 S * 8/2018 Suess ..... D9/454
2011/0092915 A1 4/2011 Olson et al.

FOREIGN PATENT DOCUMENTS

WO 2010104779 9/2010
WO 2011109205 9/2011
WO 2013032779 3/2013
WO 2014062488 4/2014

OTHER PUBLICATIONS

Schreiner Group—New Labels with Tamper-Evident and Non-Slip Features Help Enhance Patient Safety(URL: http://www.schreiner-group.com/3/company/press-room/schreiner-medipharm-us/new-labels-with-tamper-evident-and-non-slip-features-help-enhance-patient-safety/).
Unpublished Design U.S. Appl. No. 29/449,492, Eli Lilly and Company, entitled "Automatic Injection Device" filed Mar. 15, 2013.

* cited by examiner

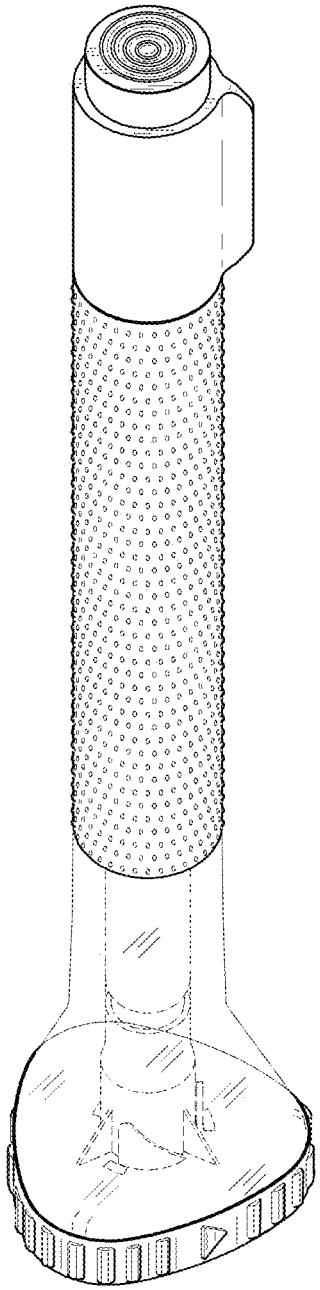
*Fig. 1*
*(Amended)*

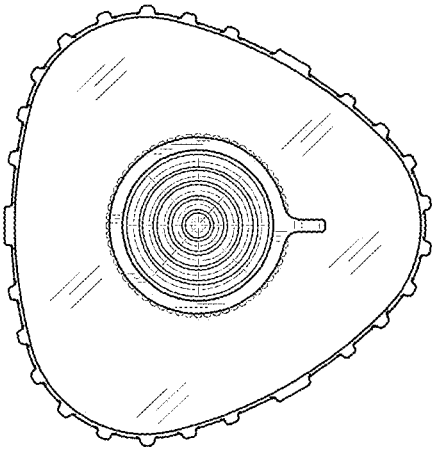
*Fig. 7*
*(Amended)*

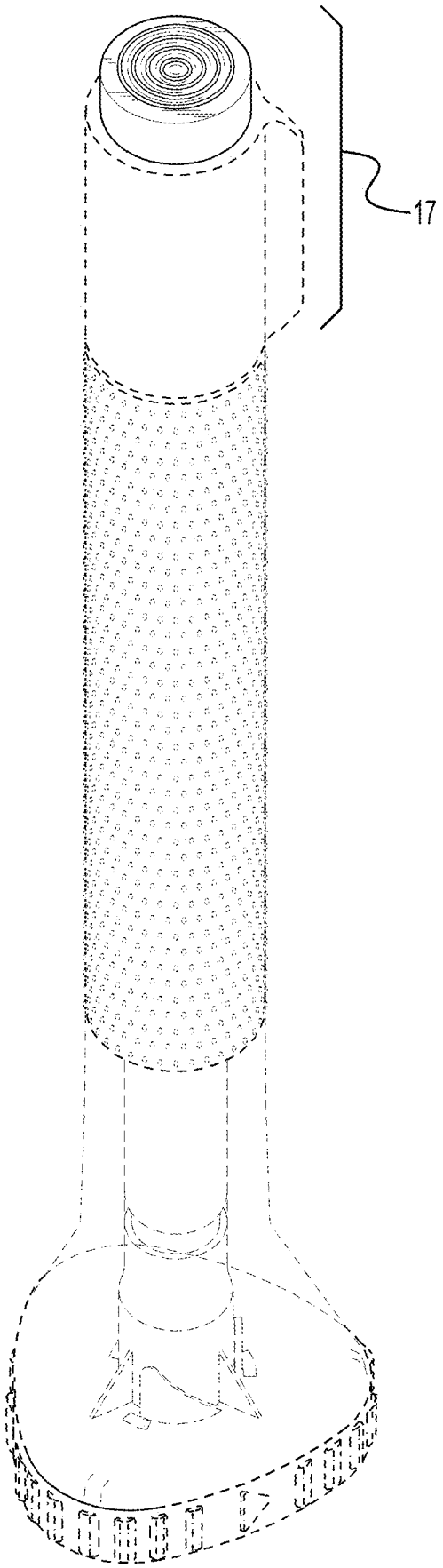
*Fig. 9*
*(New)*

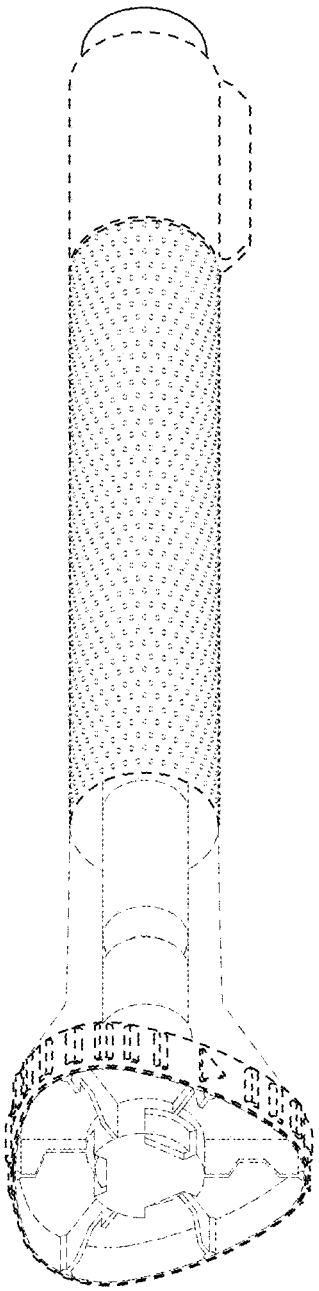
*Fig. 10 (New)*

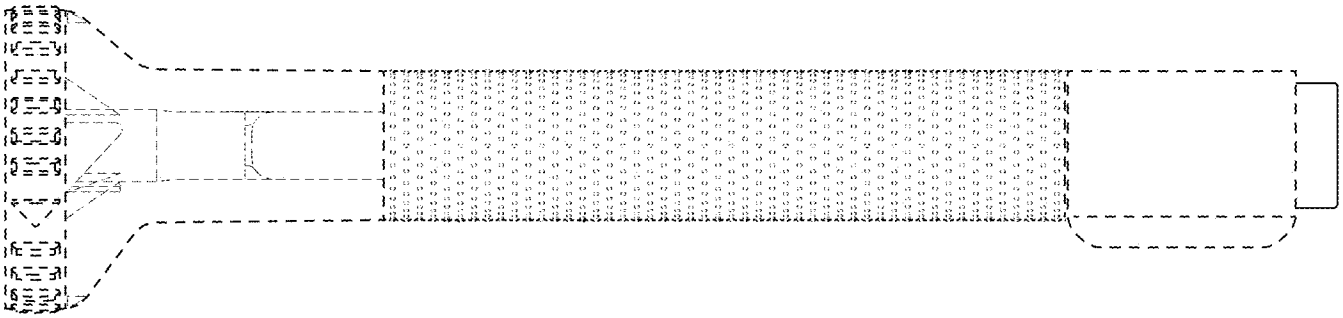
*Fig. 11 (New)*
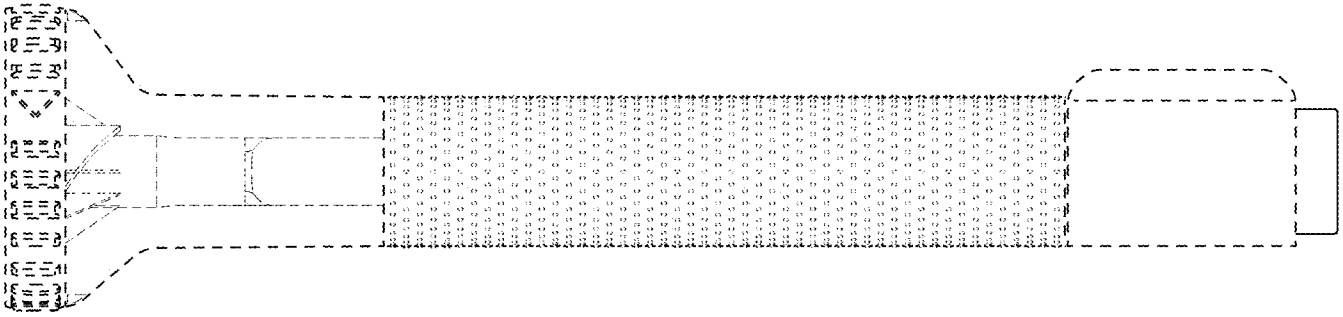
*Fig. 12 (New)*

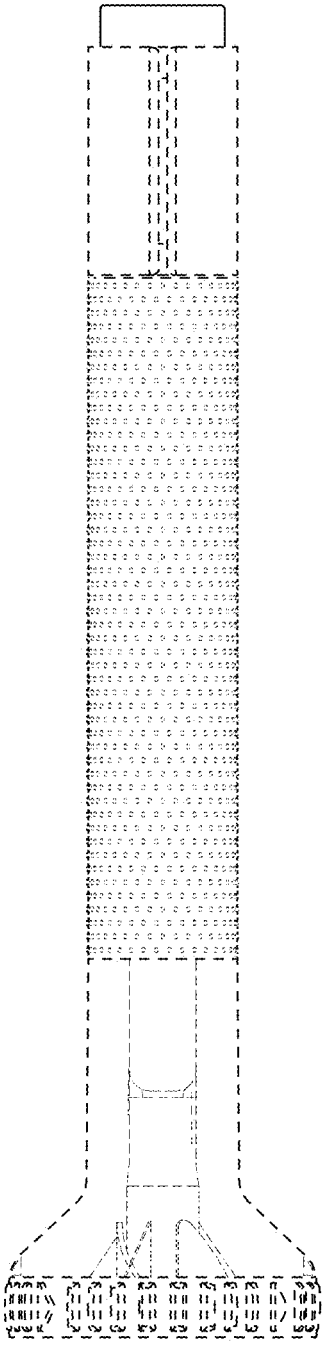
*Fig. 13 (New)*
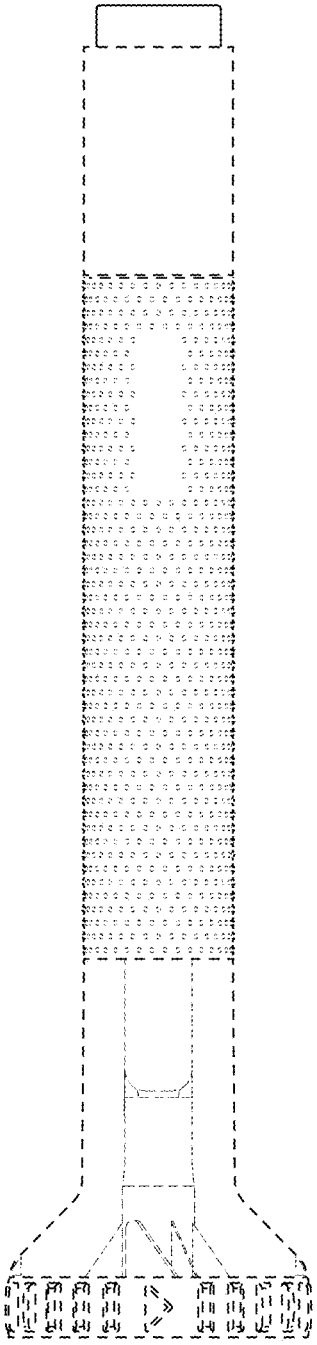
*Fig.14 (New)*

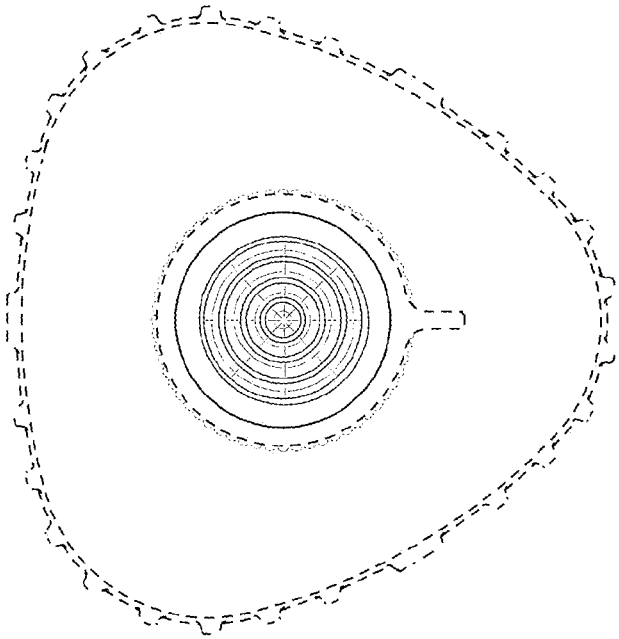
*Fig. 15*
*(New)*
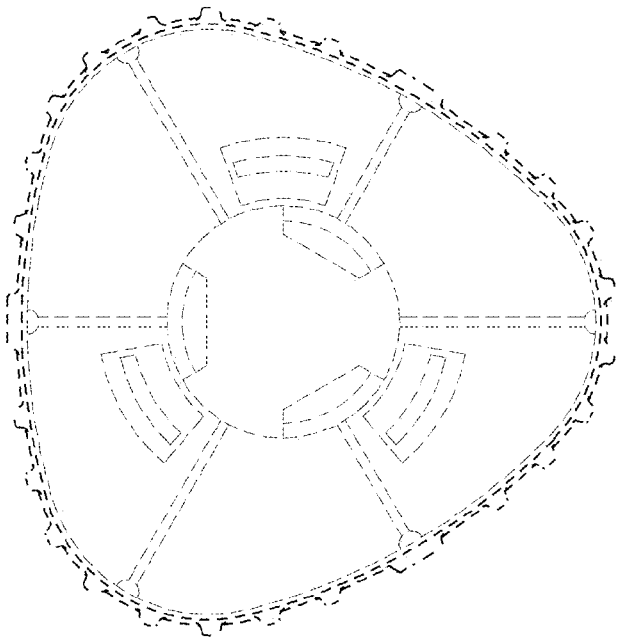
*Fig. 16*
*(New)*

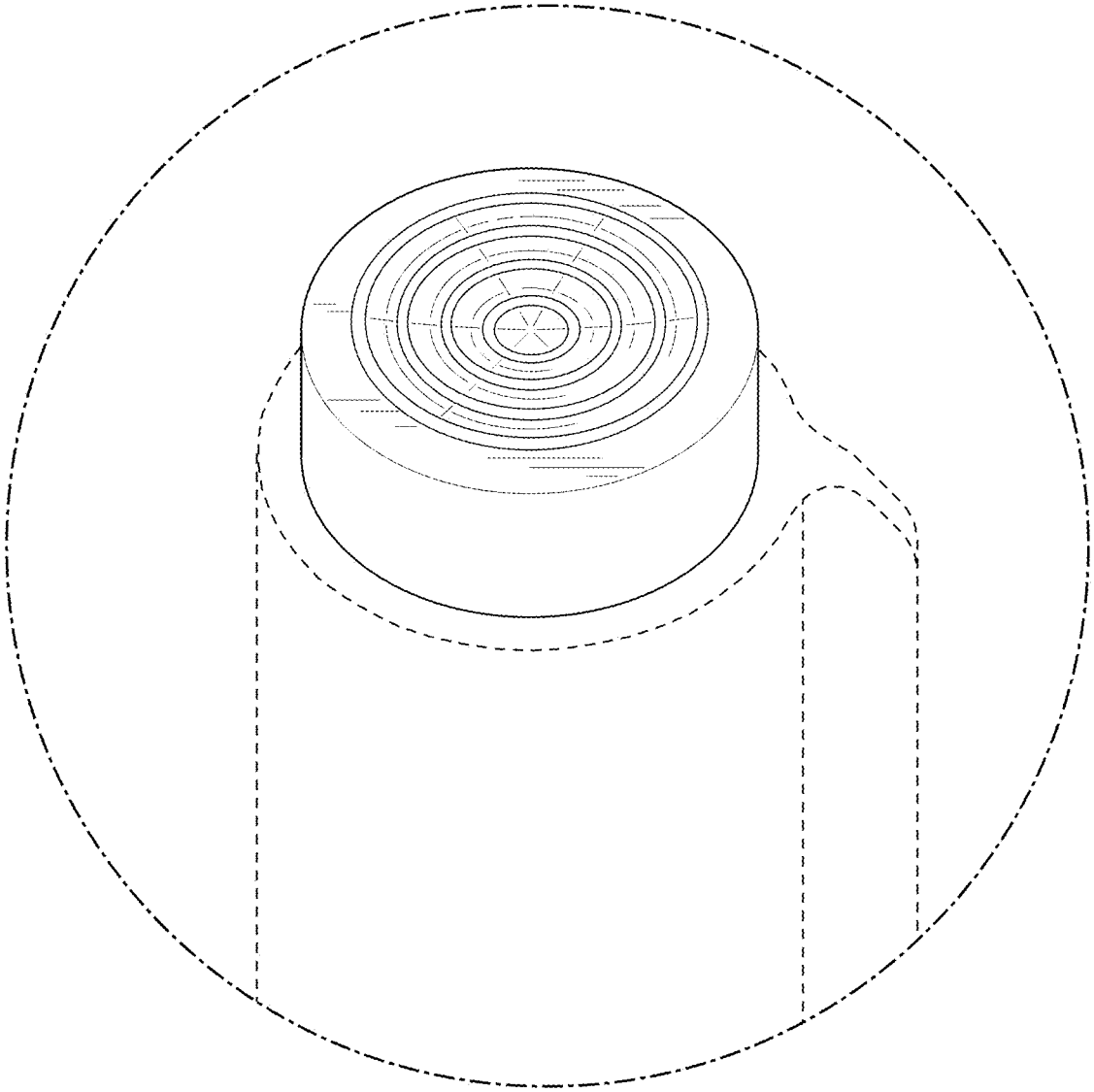
*Fig. 17*
*(New)*